United States Patent [19]
Hutchinson et al.

[11] Patent Number: 6,043,195
[45] Date of Patent: Mar. 28, 2000

[54] METHOD FOR THE ENHANCEMENT OF SEEDHEAD SUPPRESSION IN TURF

[75] Inventors: Pamela J.S. Hutchinson, Meridian, Id.; John O. Evans, Logan, Utah

[73] Assignee: American Cyanamid Company, Madison, N.J.

[21] Appl. No.: 09/033,727

[22] Filed: Mar. 3, 1998

[51] Int. Cl.[7] ............................. A01N 37/10; A01N 43/50
[52] U.S. Cl. ............................................. 504/130; 504/253
[58] Field of Search ..................................... 504/130, 253

[56] References Cited

U.S. PATENT DOCUMENTS

| | | | |
|---|---|---|---|
| 5,340,791 | 8/1994 | Bhalla et al. | 504/130 |
| 5,696,024 | 12/1997 | Szamosi et al. | 504/139 |

OTHER PUBLICATIONS

Western Society of Weed Science, 1996 Research Progress Report, p. 117.

Hopkins, William L. Global Herbicide Directory, 1st ed. "Cadre". p. 18, 1994.

Murphy, T. R. CROPU database abstract 97–84187 of "Evaluation of AC–263,222 on grass roadsides". Proc. South. Weed Sci. Soc. 49th meeting. p. 128, 1996.

*Primary Examiner*—S. Mark Clardy
*Attorney, Agent, or Firm*—John W. Hogan, Jr.

[57] ABSTRACT

There are provided a method for improving seedhead suppression and growth reduction in turfgrass which comprises applying to the turfgrass an imidazolinone herbicide in combination with dicamba and a composition therefor.

7 Claims, No Drawings

METHOD FOR THE ENHANCEMENT OF SEEDHEAD SUPPRESSION IN TURF

This application claims priority from copending provisional application Ser. No. 60/073,759, filed on Mar. 5, 1997.

BACKGROUND OF THE INVENTION

Management of turfgrass, including unimproved turfgrass, requires a substantial annual investment in time, labor, mechanical and chemical treatments, fertilization and machinery. A significant portion of the investment in turfgrass management is devoted to labor costs and the cost associated with purchasing, maintaining and operating maintenance equipment. Further, renovation of native prairiegrass and release of native grasses in range and meadowlands from competition of undesirable plant species has become a challenge of increasing importance. Therefore, the development and use of chemical treatments which suppress seedheading and reduce growth in turfgrass, control undesirable weeds in the presence of turfgrass, are not injurious to turfgrass and do not alter the appearance of turfgrass, could significantly reduce the overall maintenance costs for turfgrass management.

Recent advances in the fields of herbicide treatment and plant growth regulant agents have resulted in the discovery that certain imidazolinone compounds are particularly suitable for use on turfgrass. For example, compositions comprising imidazolinone compounds which are suitable for use in turfgrass management for lawns, sport fields, playgrounds, parks, golf courses, cemeteries and the like are described in U.S. Pat. No. 5,340,791. Further, U.S. Pat. No. 4,957,536 and U.S. Pat. No. 4,638,068 disclose growth regulant and herbicidal properties of the family of imidazolinone compounds which are suitable for use in crop cultivation practice. However, improved turfgrass management methods which provide an alternative to mechanical mowing without causing permanent grass damage or shortening stand life and which are applicable to grand spanses of prairieland, rangeland and meadowland are still being sought.

It is an object of this invention to provide an improved method to enhance seedhead suppression and growth reduction in turfgrass.

It is another object of this invention to provide turfgrass management compositions suitable for use in suppressing seedheading and reducing growth of turfgrass without causing permanent grass damage or shortening stand life.

It is a feature of this invention that many desirable wildflower and legume species are tolerant to the inventive methods and composition.

It is another feature of this invention that native prairiegrass renovation and release may be implemented with effective turfgrass management practices.

These and other objects and features of the invention will become apparent from the detailed description set forth below.

SUMMARY OF THE INVENTION

The present invention provides a method for the enhancement of seedhead suppression and growth reduction in turfgrass which comprises applying to the foliage of the turfgrass or to the soil or water in which the turfgrass is growing or to be grown an effective amount of 2-(4-isopropyl-4-methyl-5-oxo-2-imidazolin-2-yl)-5-methylnicotinic acid (IMNA) in combination with an effect-enhancing amount of 3,6-dichloro-2-methoxybenzoic acid (dicamba).

Also provided is a composition for enhancing the seedhead suppression and growth reduction in turfgrass which comprises an agriculturally acceptable solid or liquid diluent, an effective amount of 2-(4-isopropyl-4-methyl-5-oxo-2-imidazolin-2-yl)-5-methylnicotinic acid (IMNA) and an effect-enhancing amount of dicamba.

DETAILED DESCRIPTION OF THE INVENTION

The term turfgrass embraces a large body of plants of the family of gramineae. This plant family is one of the most widely distributed families found over the land surface of the globe, in marshes, in deserts, in prairies and in woodland, on sand, rocks and fertile soil, from the Tropics to the polar regions and from sea level to the perpetual snow covered mountaintop. Turfgrass, in particular, can be found in a large variety of non-cropland areas, for instance, lawns, parks, recreation areas, gardens, roadsides and railroad, utility, pipeline, and highway rights-of-way, railroad crossings, utility plant sites, petroleum tank farms, pumping installations, non-agricultural fence rows, storage areas, non-irrigation ditchbanks, prairie sites, airports, conservation reserve program (CRP) land and the like. Management of turfgrass in non-cropland areas can be costly and perpetually demanding.

It has now been found that imidazolinone compounds which include, but are not limited to, imazapyr, imazethapyr, imazaquin, imazamox, 2-(4-isopropyl-4-methyl-5-oxo-2-imidazolin-2-yl)-5-methylnicotinic acid (IMNA) and the like, preferably IMNA, when applied in combination, either concurrently or sequentially, with dicamba to turfgrass enhances seedhead suppression and reduces growth in the turfgrass. The combination of imidazolinone and dicamba, preferably IMNA and dicamba, may be applied individually or as a tank-mixed combination. In one embodiment of the invention, seedhead suppression and growth reduction in turfgrass may be enhanced by applying to the foliage of the turfgrass, or to the soil or water in which it is growing is to be grown, an effective amount of IMNA in combination with an effect-enhancing amount of dicamba.

The effective amount of IMNA and the effect-enhancing amount of dicamba will vary according to conditions such as weather, time of application, vitality and variety of grass species, vigor and size of the stand, topology of the site, and the like. In general, an effective amount of IMNA may be obtained when applied at rates of about 0.03 kg/ha to 0.25 kg/ha, preferably about 0.12 kg/ha to 0.19 kg/ha and an effect-enhancing amount if dicamba may be obtained when applied at rates of about 0.20 kg/ha to 0.50 kg/ha, preferably about 0.35 kg/ha to 0.45 kg/ha.

Turfgrass suitable for use in the method of invention includes all non-crop monocot plant species, including, but not limited to, those species shown in the table below, preferably wheatgrass such as Crested wheatgrass, Intermediate wheatgrass, Western wheatgrass and the like.

TABLE

| Common Name | Scientific Name |
| --- | --- |
| Tall fescue | *Festuca arundinacea* |
| Meadow fescue | *Festuca elatior* |

TABLE-continued

| Common Name | Scientific Name |
| --- | --- |
| Reed canarygrass | Phalaris arundinacea |
| Orchardgrass | Dactylis glomerata |
| Bahiagrass | Paspalum notatum |
| Bermudagrass | Cynodon dactylon |
| Centipedegrass | Eremochloa ophiuroldes |
| Kentucky bluegrass | Poa pretensis |
| Big bluestem | Andropogon gerardii |
| Bushy bluestem | Andropogon glomeratus |
| Little bluestem | Andropogon scoparius |
| Broomsedge | Andropogon virginicus |
| Kearny (Plains) Threeawn | Aristida longespica |
| Prarie Threeawn | Anstida oligantha |
| King Ranch Bluestem | Bothniochloa ischaemum |
| Silver Beard Bluestem | Bouteloua saccharoides |
| Sideoats grama | Bouteloua curtipendula |
| Blue grama | Bouteloua gracilis |
| Buffalograss | Buchloa dactyloides |
| Fingergrass, Rhodes grass | Choris spp. |
| Indiangrass | Sorghastrum nutans |
| Needlegrass | Stipa spp. |

Advantageously, the method of invention may be selective toward many desirable wildflower and legume species and may be employed for the establishment and maintenance of wildflower beds, for prairie or roadside-type plantings or on conservation reserve program land. The method of invention is also suitable for use in native prairiegrass renovation and release programs.

The present invention also provides a composition for enhancing seedhead suppression and growth reduction in turfgrass which comprises an agriculturally acceptable solid or liquid diluent, an effective amount of IMNA and an effect-enhancing amount of dicamba.

Effective amounts of IMNA suitable for use in the inventive composition include those amounts sufficient to provide about 0.03 kg/ha to 0.25 kg/ha, preferably 0.12 kg/ha to 0.19 kg/ha, of IMNA when applied to turfgrass and an effect-enhancing amount of dicamba suitable for use in the inventive composition include those amounts sufficient to provide about 0.20 kg/ha to 0.50 kg/ha, preferably 0.35 kg/ha to 0.45 kg/ha, when applied to turfgrass.

The composition of the invention may take the form of any conventional agricultural formulation such as an aqueous solution, liquid concentrate, concentrated emulsion, emulsion concentrate, dispersible granular, wettable powder, soluble granular and the like.

In order to facilitate a further understanding of the invention, these examples are merely illustrative and are not understood to limit the scope or underlying principles of the invention in any way. Indeed, various modifications of the invention, in addition to those shown and described herein, will become apparent to those skilled in the art from the following examples and the foregoing description. Such modifications are also intended to fall within the scope of the appended claims.

EXAMPLE 1

Evaluation Of Seedhead Suppression And Growth Reduction Of Crested Wheatgrass

In this experiment the soil type was a Parlo silt loam with 7.9 pH and an organic matter content of less than 3%. The experimental design was a randomized complete block with three replications. Individual treatments were applied to 10 by 30 foot plots with a $CO_2$ backpack sprayer using flatfan 8002 nozzles providing a 10 foot spray width calibrated to deliver 25 gpa at 39 psi. The grasses at the site were 85% crested wheatgrass, 10% downy brome and 5% bulbous bluegrass. Active ingredients are applied alone or in tank-mixed combinations. The aqueous formulations used are shown below.

| Active Ingredient | Formulation | Manufacturer |
| --- | --- | --- |
| IMNA[1] | 2 lb/gal AS | American Cyanamid |
| Dicamba[2] | 4 lb/gal AS | Sandoz |

Visual evaluations are taken at regular intervals and recorded. The mean values for evaluation recorded at 3 months after treatment are shown in Tables I and II.

Seedhead suppression for all treatments was found to be a significant season-long when compared to the untreated check. Seedhead suppression increased significantly when the 5-methylnicotinic acid derivative was applied in combination with dicamba as compared to when the 5-methylnicotinic acid derivative was applied alone.

[1] PLATEAU®-2-—(4-isopropyl-4-methyl-5-oxo-2-imidazolin-2-yl)-5-methylnicotinic acid
[2] BANVEL®

TABLE I

Evaluation of Growth Reduction Of Treated Crested Wheatgrass At 3 Months After Treatment

| Treatment | Rate | Rate (kg/ha) | % Decreased Plant Height |
| --- | --- | --- | --- |
| A | 0.10 | — | 37.3 |
| A + Dicamba | 0.10 | 0.42 | 40.5 |
| A | 0.14 | — | 48.3 |
| A + Dicamba | 0.14 | 0.42 | 57.7 |
| A | 0.17 | — | 51.7 |
| A + Dicamba | 0.17 | 0.42 | 51.7 |
| A | 0.21 | — | 58.0 |
| A + Dicamba | 0.21 | 0.42 | 60.7 |

TABLE II

Evaluation Of Seedhead Suppression Of Treated Crested Wheatgrass At 3 Months After Treatment

| Treatment | Rate (kg/ha) | Rate (kg/ha) | % Seedhead Suppression |
| --- | --- | --- | --- |
| A | 0.10 | — | 65.0 |
| A + Dicamba | 0.10 | 0.42 | 82.5 |
| A | 0.14 | — | 78.3 |
| A + Dicamba | 0.14 | 0.42 | 85.0 |
| A | 0.17 | — | 70.0 |
| A + Dicamba | 0.17 | 0.42 | 90.0 |
| A | 0.21 | — | 83.3 |
| A + Dicamba | 0.21 | 0.42 | 91.7 |

What is claimed is:

1. A method for the enhancement of seedhead suppression and growth reduction in turfgrass which comprises applying to the foliage of the turfgrass or to the soil or water in which the turfgrass is growing or to be grown an effective amount of 2-(4-isopropyl-4-methyl-5-oxo-2-imidazolin-2-yl)-5-methyinicotinic acid in combination with an effect-enhancing amount of dicamba wherein said effect-enhancing amount is about 0.35 to 0.45 kg/ha.

2. The method according to claim 1 wherein the 2-(4-isopropyl-4-methyl-5-oxo-2-imidazolin-2-yl)-5-methylnicotinic acid is applied at a rate of about 0.030 kg/ha to 0.25 kg/ha.

3. The method according to claim 2 wherein the effective amount of said nicotinic acid is about 0.12 kg/ha to 0.19 kg/ha.

4. The method according to claim 1 wherein the turfgrass is unimproved turfgrass.

5. The method according to claim 4 wherein the unimproved turfgrass is selected from the group consisting of tall fescue, bahiagrass, wheatgrass, bluegrass, bermudagrass, centipedegrass and prairiegrass.

6. The method according to claim 5 wherein said turfgrass is wheatgrass.

7. The method according to claim 6 wherein the wheatgrass is Crested wheatgrass or Western wheatgrass.

* * * * *